United States Patent [19]

Matthews et al.

[11] Patent Number: 4,816,259

[45] Date of Patent: Mar. 28, 1989

[54] PROCESS FOR COATING GELATIN CAPSULES

[75] Inventors: James W. Matthews, Millburn; Gerald Vergilio, Rahway, both of N.J.

[73] Assignee: Chase Chemical Company, L.P., Newark, N.J.

[21] Appl. No.: 13,600

[22] Filed: Feb. 12, 1987

[51] Int. Cl.$^4$ .............................................. A61K 9/48
[52] U.S. Cl. ...................................... 424/463; 427/3; 427/214; 427/220; 427/221
[58] Field of Search .................... 424/456, 463; 427/3, 427/214, 220, 221; 514/962, 960

[56] References Cited

U.S. PATENT DOCUMENTS

| | | | |
|---|---|---|---|
| 3,197,369 | 7/1965 | Widmann et al. | 167/64 |
| 3,256,111 | 6/1966 | Singiser | 427/3 |
| 3,432,594 | 3/1969 | Bauer et al. | 424/33 |
| 3,592,945 | 7/1971 | Eugelking et al. | 252/316 |
| 3,653,934 | 4/1972 | Rolle | 106/125 |
| 3,656,997 | 4/1972 | Cordes | 424/463 X |
| 3,870,702 | 3/1975 | Koyanagi et al. | 514/960 X |
| 3,959,540 | 5/1976 | Leiberich et al. | 428/35 |
| 4,017,647 | 4/1977 | Ohno et al. | 424/463 |
| 4,138,013 | 2/1979 | Okajima | 206/528 |
| 4,335,099 | 6/1982 | Funakoshi et al. | 424/496 X |
| 4,372,974 | 2/1983 | Fish et al. | 514/561 |
| 4,385,078 | 5/1983 | Onda et al. | 427/3 |

FOREIGN PATENT DOCUMENTS

| | | | |
|---|---|---|---|
| 53-139715 | 12/1978 | Japan | 427/3 |
| 57-50915 | 3/1982 | Japan | 424/463 |
| 7514012 | 6/1976 | Netherlands | 424/463 |

OTHER PUBLICATIONS

CA96(26):223288h Chemical Abstracts.
CA105(24):2;4003p Chemical Abstracts.

*Primary Examiner*—Shrive P. Beck
*Attorney, Agent, or Firm*—Christel, Bean & Linihan

[57] ABSTRACT

This invention provides a new gelatin capsule formulation and subcoating for producing soft gelatine capsules having better mechanical strength and an improved capacity for adhering to known coating compositions, particularly enteric coating compositions. The finished capsule shell formulation comprises gelatin 65%–70%, glycerin 22%–25% and water 8%–10% and the subcoating is a suspension of hydroxypropyl methylcellulose. The subcoating may also be used to manufacture improved enteric coated hard gelatin capsules.

16 Claims, No Drawings

PROCESS FOR COATING GELATIN CAPSULES

This invention relates to a process for coating gelatin capsules commonly used to encapsulate solid, semi-solid and liquid dosage forms. More particularly, this invention relates to a process for applying a coating composition, such as a known enteric coating composition, to a soft gelatin capsule shell, wherein the resulting capsule will not crack, undergo substantive deformation, or leak its contents during standard large scale capsule manufacturing procedures, and wherein it will remain essentially stable until used for its intended purpose.

BACKGROUND OF THE INVENTION

The coating of solid dosage forms such as tablets and pills has long been known in the prior art. Coatings are commonly applied to such dosage forms for one or more of the following reasons: to protect the ingredients against the atmosphere, to mask unpleasant taste and odor, to improve the appearance of uncoated tablets and pills, to control the site of action of the drug and to prevent incompatabilities when two or more pharmaceutically active ingredients are incorporated into a single dosage form. Numerous coating solutions are powders have been used over the years in the coating of tablets including polymers or acrylic acid or acrylic acid derivatives as well as other polymeric substances, such as shellac, cellulose derivatives, polyvinylpyrrolidone, polyethyleneglycol, copolymers or polyvinylpyrrolidone and polyvinylacetate, silicon resins and the like. Although the coating of tablets and pills can be effected relatively easily by known processes owing to their porous surfaces which readily adhere to such coating substances, difficulties arise when coating soft gelatin capsules because of their smooth, nonabsorptive surfaces and flexibility or elasticity.

Many attempts have been made to produce improved coating capsules. In particular, several attempts have been made to produce stable enteric coated soft gelatin capsules which resist dissolution in the acid secretions of the stomach and dissolve or disintegrate primarily in the alkaline secretions of the intestines.

Enteric coated soft gelatin capsules are desirable for the administration of liquid medications which are distasteful to the patient, or for drugs which cause nausea or gastric distress, or which are unstable in the acid environment of the stomach. In addition, enteric coatings are useful for producing a delayed action of a drug or to deliver medication to the intestinal tract when this is the intended site of action.

Accordingly, a main object of the present invention is to provide a new process for enterically coating soft gelatin capsules which exhibit superior mechanical strength, and improved environmental stability.

SUMMARY OF THE INVENTION

It has now been discovered that soft gelatin capsules (softgels) formulated to contain specific compositional ranges of gelatin, glycerin and water provide an improved capsule shell surface having a sufficient hardness for receiving successive coatings of polymeric materials and other known coating compositions. It has further been discovered that such capsules exhibit an improved mechanical strength and will not crack or undergo substantial deformation during standard large scale capsule manufacturing procedures. Moreover, the coatings applied to capsules produced in accord with this invention are stable and adhere to the surface of the capsule without cracking or flaking off during the manufacturing process.

It has further been discovered that by applying to the outer surface of the soft gelatin capsule at least one continuous layer of a subcoating hydroxypropyl methylcellulose to an added weight of 8%-10%, the surface of the capsule exhibits an improved capacity for adhering to known enteric coating compositions.

DETAILED DESCRIPTION OF THE INVENTION

Capsules according to the instant invention are produced by admixing 43%-46% gelatin, 16%—18% glycerin and 38%-39% water into a wet mass which is thereafter manufactured into finished capsules containing 65%-70% gelatin, 22%-25% glycerin and 8%-10% water, using conventional capsule manufacturing procedures and equipment.

During the production of the wet gelatin mass for the preparation of the capsules, conventional additives, including plasticizers, coloring agents, opacifiers, fillers and preservatives such as parabens, may optionally be added to the formulation without causing any detrimental effects to the finished soft gelatin capsule.

The gelatin mass is prepared in a manner that produces a smooth completely dispersed gelatin suspension. The gelatin required for this dispersion should preferably be between 130 bloom and 200 bloom alkali based skin or bone type, approved for food use or of U.S.P. quality. The glycerin used should be of U.S.P. quality and the water should be approved for drug use (U.S.P.).

The capsules are manufactured on standard commercial encapsulating equipment. The capsules produced thereby are cleaned and dried using standard techniques to produce an end product which is hard, evenly shaped and which exhibits no shell weak points either internally or externally.

The soft gelatin capsules thus produced are thereafter placed in a conventional device known to permit the continuous tumbling of the capsules, which facilitates the application of all the coating materials herein described.

After the capsules are air dried, any one of several known coating solutions may optionally be applied to the capsule shell to improve its surface appearance or to render the capsule moisture proof. For example, a coating of confectioners glaze (food grade shellac) dissolved in alcohol may be applied in an amount sufficient to completely cover all surfaces of the capsules. About one to three applications of glaze are usually sufficient to insure adequate dryness, but more or less may be applied. The capsules are again air dried to remove the alcohol solvent.

The process for coating the gelatin capsules according to this invention requires an initial application of a subcoating onto the outer surface of the capsule shell. The subcoating comprises a suspension of hydroxypropyl methyl cellulose in water to which a small amount of polyethylene glycol is added. The amount of hydroxypropyl methyl cellulose present in the suspension is between about 4%-9%, with a trace-1% of polyethylene glycol. A typical formulation contains 7% hydroxypropyl methyl cellulose, 1% polyethylene glycol and the remainder water.

The subcoat layer is applied to the capsules by continuous spraying techniques until an added weight of between 8% to 10% is achieved. The moisture content of the coating should be between 3% and 5% by weight.

The layers of the subcoating are preferably applied using spraying equipment which permits a partially dry mist to be sprayed on the surface of the capsule at a rate such that the amount of solvent applied is essentially equal to the amount of solvent evaporating. The drying process may be accelerated by the simultaneous injection of warm air at a temperature below the distortion temperature of the capsule shell (i.e. about 75° C.). This insures that the capsule shell will not undergo any significant deformation during the coating and manufacturing process.

After the subcoated capsules are dried sufficiently, any one of several known tablet coatings may be applied to the capsules as for example: waterproofing and sealing compounds, smoothing compounds, coloring and finishing compounds, polishing compounds, cellulose polymer film compositions, compression coating compositions, and entering coating compounds. However, since enteric coated capsules are of particular interest to the pharmaceutical industry, the remainder of the specification will be directed to the application of an enteric coating composition.

There are several known enteric coating substances which include fats, fatty acids, waxes and mixtures, shellac, ammoniated shellac, cellulose acetate phthalates, and various other polymers and co-polymers containing methacrylic acid and methacrylic acid alkyl esters and related compositions.

A preferred enteric coating composition which may be applied to the capsules of this invention has the following formula:

| Polyvinyl acetate phthalate | 12%–18% |
| Ammonium hydroxide (conc.) | 0.25%–0.35% |
| Water U.S.P. qs | 100% |

In an suitable container the enteric polymer is mixed with an appropriate amount of water to form an even dispersion. The ammonium hydroxide is added to this dispersion with adequate mixing. The enteric coating mixture is sprayed onto the capsules using the same type of equipment described for use with the subcoating application. The rate of spraying and the temperature of the drying air will also be essentially the same as that used in the subcoating step.

The above process describes the application of an enteric coating to a soft gelatin capsule. Soft gelatin capsules as defined herein are elastic, globular, gelatin shells containing sufficient glycerin to retain permanent flexibility. Hard gelatin capsules are made largely from gelatin and sugar, the U.S.P. permitting the gelatin used for this purpose to contain 0.15% sulfur dioxide to prevent decomposition during manufacture. Hard gelatin capsules contain about 9%–12% water but this may vary depending on storage conditions.

In accord with this invention it has further been discovered that the subcoating described herein for use with soft gelatin capsules, may also be used to improve the surface adherence characteristics of hard gelatin capsules, thereby making it possible to produce a superior enteric coated hard capsule.

The following Examples will serve to further illustrate the invention:

EXAMPLE I

Enteric Coated Soft Gelatin Capsules

Soft capsules for enteric coating are manufactured from gelatin mass by wetting the 150 bloom gelatin with U.S.P. glycerin (17%) and purified water U.S.P. (37%) in a jacketed vacuum vessel. Heat (150° F.) and vacuum (28 Hg) are applied. The deaerated, melted gelatin mass is maintained in a liquid state by the use of a heated container. The heated liquid gelatin is used to manufacture a gelatin sheet on a continuous basis. The gelatin sheet is processed on a rotary die soft gelatin capsule machine into liquid filled soft gels. The capsules must be manufactured in such a way to provide a full and continuous seal at the time of manufacture. The gelatin film must be of adequate thickness to provide a minimum of 0.018" dry wall thickness. The capsules are dried tin such a manner as to have a finished moisture content of the capsule shell of 9.0%. The finished, dried capsules must be completely free of any oily residues.

Twelve (12) kg. of dried cleaned capsules are placed into a 24" Accela-Cota or other similar tumbling device. While tumbling at approximately 14 R.P.M., 120 ml of 5 lbs. confectioners glaze is applied to the tumbling capsules. Care must be taken not to apply more glaze than is required to just completely cover all the surfaces of the capsules. The capsules are allowed to tumble with warm air passing over the tumbling capsules. The temperature of the air should be approximately 75° C. When the capsules are completely dry, the glaze application and drying procedure are repeated. The glazed capsules are then removed from the coating device and allowed to dry 16 to 24 hours on trays or on other similar devices. In an appropriate container 795.0 gm of hydroxypropyl methyl cellulose U.S.P. (Pharmacoat 615/methocel E15 LV premium or similar quality material) is mixed with 10,433.0 gm of purified water U.S.P. and 113.0 gm of polyethylene glycol 3350 U.S.P. The mixture is stirred until a clear solution is obtained. Using a peristaltic pump feeding at the rate of 50 ml/minute, the subcoating solution is sprayed on the capsules tumbling in the coating device. The solution is atomized using a Binks spray gun model 610 or similar device with a #66 tip and 35 p.s.i. atomizing air. The temperature of the drying air should be 75° C. while the capsules are being sprayed. The subcoat solution is sprayed on the capsules until a weight increase of 8% is achieved. The capsules are allowed to tumble slowly until thoroughly dry. In an appropriate container, 1700.0 gm of polyvinyl acetate phthalate is mixed with purified water and 228 gm of polyethylene glycol 3350. After mixing for about thirty minutes, 35 gm of concentrated ammonium hydroxide solution (reagent grade) is added to this mixture and remixed for an additional ten minutes. (Optionally, cellulose acetate phthalate latex suspension may be used in place of the polyvinyl acetate phthalate. Other plasticizer systems may be used in conjunction with this alternative enteric forming polymer.)

Using the spray equipment described above for the application of the subcoating solution, the enteric polymer suspension is sprayed on the tumbling capsules until the capsules have gained 8% additional weight. The enteric capsules are then submitted to the laboratory for "enteric coating testing". After the capsules have been approved by the laboratory, they are again sprayed with a layer of the subcoating solution described above until a 1% weight gain has been achieved.

Coloring agents consisting of FD&C or D & C dyes are pigments (titanium dioxide) may be added to the subcoating and/or the enteric coating to color the capsules. The capsules can be marked using various printing equipment supplied commercially by the Hartnett Co. of Philadelphia or the Markem Co. of Keene, NH. This should be done at the end of the coating procedure.

EXAMPLE II

Enteric Coated Hard Gelatin Capsules

Hard gelatin capsules to be enteric coated are prepared using a high bloom gelatin. The empty capsule shells are obtained commercially from suppliers whose empty shells possess a mechanical locking device on the capsule to prevent opening of the capsule after it has been filled. The dry active ingredient is mixed with inert fillers in such a manner as to allow the maximum fill to be placed in empty capsule shell. This is accomplished by the use of various capsule filling machines such as Parke Davis or Lilly ring filling machines or Hafflinger & Karg or Zanasi type automatic capsule filling machine. The filled capsules must be completely closed and locked. The capsules are cleaned using any method which produces a particle free surface with no oil or other contaminants on the surface of the capsule.

Twelve (12) kg. of clean hard gelatin capsules are placed into a 24" Accela-Cota or similar tumbling device. Approximately 120 ml of 3 lbs. confectioners glaze (food grade shellac) are applied to the tumbling capsules. Care must be taken to completely cover the capsule surface. Warm air about 75° C. is applied to the tumbling capsules. The capsules are allowed to tumble in the warm air until the capsules are free of all volatile solvents. The capsules are then removed from the coating device and air dried for 16 to 24 hours on trays or on other similar devices.

In an appropriate container 795.0 gm of hydroxypropylmethyl cellulose U.S.P. (Pharmacoat 615/methocel E15 LV premium or similar quality material) is mixed with in 10,433.0 gm of purified water U.S.P. and 113.0 gm of polyethylene glycol 3350 U.S.P. The mixture is stirred until a clear solution is obtained. Using a peristaltic pump feeding at the rate of 50 ml/minute, the subcoating solution is sprayed on the capsules tumbling in the coating device. The solution is atomized using a Binks spray gun model 610 or similar device with a #66 tip and 35 P.S.I. atomizing air. The temperature of the drying air should be 75° C. while the capsules are being sprayed. The subcoating solution is sprayed on the capsules until a weight increase of 8% is achieved. The capsules are allowed to tumble slowly until thoroughly dry.

In an appropriate container, 1700.0 gm of polyvinyl acetate phthalate is mixed with 11,400 gm of purified water and 228 gm of polyethylene glycol 3350, and mixed for thirty minutes. 35 gm of concentrated ammonium hydroxide solution (reagent grade) is then added and the mixture is blended for about then additional minutes. (Optionally, cellulose acetate phthalate latex suspension may be used in place of the polyvinyl acetate phthalate. Other plasticizer systems may be used in conjunction with this alternative enteric forming polymer.)

Using the spray equipment described above for the application of the subcoating solution, the enteric polymer suspension is sprayed onto the tumbling capsules until the capsules have gained 8% additional weight. The enteric capsules are then submitted to the laboratory for "enteric coating testing". After the capsules have been approved by the laboratory, they are again sprayed with a layer of the subcoating solution described above until a 1% weight gain has been achieved.

Coloring agents consisting of FD&C or D & C dyes and pigments (titanic dioxide) may be added to the subcoating and/or the enteric coating to color the capsules. The capsules can be marked using various printing equipment supplied commercially by the Hartnett Co. of Philadelphia or the Markem Co. of Keene, NH. This should be done at the end of the coating procedure.

Enteric coated capsules according to this invention were subjected to disintegration tests using the method described in U.S.P. XXI (pages 1242-1243). This method consists of subjecting the capsules for one hour to the action of simulated gastric juices and then to the action of simulated intestinal juices, and in measuring the time of disintegration in the simulated intestinal juices. All of the capsules tested passed the U.S.P. criteria for enteric-coated tablets. All capsules remained intact after being subjected to the simulated gastric juices for one hour and all capsules dissolved in less than 30 minutes when subjected to the simulated intestinal juices.

Capsules formulated and coated according to the method of this invention do not crack, undergo substantial deformation, or leak their contents during large scale capsule manufacturing processes. Moreover, such capsules exhibit sufficient mechanical strength to permit them to be colored or printed upon using any known approved film forming binder or polymer such as a cellulose polymer combined with an approved coloring agent, dye or pigment.

It is fully understood that the foregoing Examples are intended to be merely illustrative and not to be construed or interpreted as being restrictive or otherwise limiting of the present invention, excepting as set forth and defined in the hereto appended claims.

We claim:

1. A process for coating a soft gelatin capsule shell suitable for encapsulating solid, semi-solid or liquid dosage forms to improve the surface characteristics of said capsule shell for receiving and adhering to one or more successive coating layers of known coating compositions, comprising applying to the outer surface of said shell at least one continuous layer of a subcoating composition consisting essentially of hydroxypropyl methyl cellulose about 4%-9%, polyethylene glycol about 0.5%-1% with the remainder water in an mount sufficient to increase the total weight of said shell by about 8%-10%, and thereafter applying one or more continuous coating layers to said shell comprising a known hard tablet coating composition selected from the group consisting of: waterproofing and sealing compounds, smoothing compounds, coloring and finishing compounds, polishing compounds, cellulose polymer film compositions, compression coating compositions, and enteric coating compounds, wherein said subcoating is applied to said capsule shell using standard spraying techniques at a temperature below the distortion temperature of the capsule shell thereby essentially eliminating deformation of the capsule shell during the manufacturing process.

2. The process of claim 1 wherein at least one layer of a suitable enteric coating composition is applied over said subcoating in an amount sufficient to cause the capsule shell to withstand U.S.P. testing criteria for enteric coated tablets.

3. The process of claim 2 wherein said enteric coating composition is selected from the group consisting of fats, fatty acids, waxes and mixtures, shellac, ammoniated shellac, and cellulose acetate phthalates.

4. The process of claim 3 wherein said enteric coating comprises an approved solution of polyvinyl acetate phthalate.

5. The process of claim 3 wherein said enteric coating comprises an approved suspension of cellulose acetate phthalate.

6. The process of claim 3 wherein said enteric coating composition comprises the following ingredients by weight: polyvinyl acetate phthalate about 12%–18%, ammonium hydroxide about 0.25%–0.35% with the remainder water.

7. A soft gelatin capsule enterically coated in accord with the process of claim 6.

8. The soft gelatin capsule of claim 7 colored or printed upon using a known approved cellulose polymer in combination with an approved coloring agent or pigment.

9. A process for coating a hard gelatin capsule to improve the surface characteristics of said capsule shell for receiving and adhering to one or more successive coating layers of known coating compositions, comprising applying to the outer surface of said capsule at lease one continuous layer of subcoating composition consisting essentially of hydroxypropyl methyl cellulose about 4%–9%, polyethylene glycol about 0.5%–1% with the remainder water in an amount sufficient to increase the total weight of said shell by about 8%–10%, and thereafter applying one or more continuous coating layers to said shell comprising a known hard tablet coating composition selected from the group consisting of: waterproofing and sealing compounds, smoothing compounds, coloring and finishing compounds, polishing compounds, cellulose polymer film compositions, compression coating compositions, and enteric coating compounds, wherein said subcoating is applied to said capsule shell using standard spraying techniques at a temperaure below the distortion temperature of the capsule shell thereby essentially eliminating deformation of the capsule shell during the manufacturing process.

10. The process of claim 9 wherein at least one layer of a suitable enteric coating composition is applied over said subcoating in an amount sufficient to cause the capsule shell to withstand U.S.P. testing criteria for enteric coated tablets.

11. The procss of claim 10 wherein said enteric coating composition is selected from the group consisting of fats, fatty acids, waxes and mixtures, shellac, ammoniated shellac, and cellulose acetate phthalates.

12. The process of claim 9 wherein said enteric coating comprises an approved solution of polyvinyl acetate phthalate.

13. The process of claim 9 wherein said enteric coating comprises an approved suspension of cellulose acetate phthalate latex.

14. The process of claim 9 wherein said enteric coating composition comprises the following ingredients by weight: polyvinyl acetate phthalate about 12%–18%, ammonium hydroxide about 0.25%–0.35% with the remainder water.

15. A hard gelatin capsule enterically coated in accord with the process of claim 14.

16. The hard gelatin capsule of claim 15 colored or printed upon using a known approved cellulose polymer in combination with an approved coloring agent or pigment.

* * * * *

UNITED STATES PATENT AND TRADEMARK OFFICE
CERTIFICATE OF CORRECTION

PATENT NO. : 4,816,259

DATED : March 28, 1989

INVENTOR(S) : James W. Matthews

It is certified that error appears in the above-identified patent and that said Letters Patent is hereby corrected as shown below:

On the title page, item [75], "Gerald Vergilio" should read
--Gerald Virgilio--.

Column 6, line 54, claim 1, "mount" should be --amount--.

Column 7, line 31, claim 9, "lease" should be --least--.

Column 8, lines 7-8, "temperaure" should be --temperature--.

Signed and Sealed this

Fourteenth Day of November, 1989

Attest:

JEFFREY M. SAMUELS

*Attesting Officer*      *Acting Commissioner of Patents and Trademarks*